US00PP08499P

United States Patent [19]

Keck, Jr.

[11] Patent Number: Plant 8,499

[45] Date of Patent: Dec. 14, 1993

[54] BRIGHTON 650 GRAPEVINE

[75] Inventor: Howard B. Keck, Jr., Thermal, Calif.

[73] Assignee: Brighton Farming Company, Thermal, Calif.

[21] Appl. No.: 633,271

[22] Filed: Dec. 24, 1990

[51] Int. Cl.[5] ..... A01H 5/00

[52] U.S. Cl. ..... Plt./47.3

[58] Field of Search ..... Plt./47, 47.3

[56] References Cited

U.S. PATENT DOCUMENTS

P.P. 3,106 4/1972 Garabedian ..... Plt. 47

P.P. 5,151 12/1983 Hahn et al. ..... Plt. 47.3

OTHER PUBLICATIONS

Carleton, R. M. "*Brighton*", *The New Vegetable & Fruit Garden Book* 1976 Henry Regnery Co., Chicago, p. 159.

*Primary Examiner*—James R. Feyrer

*Attorney, Agent, or Firm*—Worrel & Worrel

[57] ABSTRACT

A new and distinct variety of grapevine which is somewhat remotely similar to the "Superior Seedless" grapewine with which it is most closely related, but from which it is distinguished by producing fruit which are mature for harvesting and shipment approximately eleven days prior to the fruit produced by "Superior Seedless" grapevine, or approximately May 25 in the Coachella Valley of California and which has a larger, rounder berries and bunches with longer shoulders.

1 Drawing Sheet

BACKGROUND OF THE NEW VARIETY

The present invention relates to a new and distinct variety of grapevine which will hereinafter be denominated varietally as "Brighton 650" and more particularly to a grapevine which bears seedless berries which are larger and rounder than the berries of the "Superior Seedless" grapevine, the flesh of which is very firm and crisp and has excellent eating and shipping quality and which is mature for harvesting and shipment approximately May 25 near Thermal in the Coachella Valley of California.

The "Superior Seedless" grapevine has been of notable commercial success in producing seedless grapes ripening for harvest in the Coachella Valley of California approximately June 6. Horticultural experts, growers and others having an interest in the development of new commercial varieties of fruit are acutely aware that there is a market demand for new varieties which possess characteristics superior to existing varieties or which fit within ripening periods during which no comparable varieties are available. There are a multitude of other rather more subtle considerations which may have a direct bearing upon the commercial success of a variety. Size, coloration, flavor, sugar and acid content, holding quality, shipping quality, resistance to disease and still other criteria may influence market acceptance for any new variety.

The new and distinct variety of the present invention possesses a unique conbination of attributes which make it a particularly promising variety in that it fits well with existing commerical varieties having ripening dates over substantially contiguous time periods and otherwise has exceptional characteristics in the above-noted respects.

ORIGIN AND ASEXUAL REPRODUCTION OF THE NEW VARIETY

The present variety of grapevine hereof was discovered by the inventor in the spring of 1986 in his grape vineyard located near Thermal in the Coachella Valley of California. The applicant discovered the new variety as a sport of the "Superior Seedless" grapevine. While examining a second year planting of "Superior Seedless" grapevines on his property, he noticed that one cane on a single vine was blooming several days earlier than the remaining canes on the same vine and the surrounding grapevines in the immediate vicinity. He marked the vine of the new variety and continued to observe it throughout the growing season. As the fruit of the new variety grew and matured, the inventor observed that the fruit of the new variety was bigger and more rounded than that of the surrounding "Superior Seedless" grapevines. On May 25, 1986, the new variety was 15.5 bricks and 0.54 sugar acid content whereas it took until Jun. 6, 1986 for the fruit of the surrounding vines to reach the same sugar acid content.

The inventor took cuttings from the sport of the new variety and asexually reproducing the new variety by planting the cuttings so as to cause them to generate their own respective roots. The rooted cuttings were planted among some "Superior Seedless" grapevines and grew and trained them to fruiting grapevines. The inventor observed that the asexually reproduced grapevines of the new variety retained the same characteristics which caused the original sport to be selected with earlier blooming, larger bunches and earlier fruit maturity than the surrounding grapevines. The parent sport and propagated grapevines of the new variety were observed over the last two years and continue to evidence the same distinctive characteristics.

SUMMARY OF THE NEW VARIETY

The grapevine of the new variety is characterized as to novelty by producing fruit having seedless berries which are individually large and round and similarly fruit in large bunches. The fruit ripens for commercial harvesting approximately May 25 and holds for continued harvest until about June 20 near Thermal in the Coachella Valley of California. The new variety is most closely similar to the "Superior Seedless" grapevine from which it was derived as a sport, but from which it is distinguished and characterized principally as to novelty by producing larger, rounder berries which are ripe for harvesting approximately eleven days earlier than those of the "Superior Seedless" grapewine. This comparison between the grapevine of the new variety and the "Superior Seedless" grapevine is based upon close observation of both varieties of the same age grown side-by-side on their own respective root stocks, under identical cultural conditions and treatments. In neither case were chemical agents applied to the varieties of grapevine.

BRIEF DESCRIPTION OF THE DRAWING

The accompanying drawing is a color photograph of clusters of grapes of the new variety showing their appearance sufficiently mature for harvesting and shipment; several leaves showing their dorsal and ventral coloration; a typical section of vine; and several berries halved in the axial plane to display the flesh coloration thereof, all of the new variety.

DETAILED DESCRIPTION

Referring more specifically to the pomological details of this new and distinct variety of grapevine, the following has been observed under the ecological conditions prevailing at the grape vineyard of the inventor located near Thermal in the Coachella Valley of California. All major color code designations are by reference to the Dictionary of Color, by Maerz and Paul, Second Edition, published in 1950. Common color names are also occasionally employed.

VINE

Generally:

*Vigor.*—Vigorous.

*Figure.*—Upright; dense; hardy.

*Productivity.*—Very productive. From the third bud from the base of the fruiting canes and higher are usually sixty-five percent (65%) fruitful or more. There is no tendency to produce a small second crop of clusters on current season's growth.

Trunk:

*Size.*—Large and stocky.

*Bark.*—Loose and shreddy.

Canes:

*Size.*—Long.

*Numbers.*—Numerous.

*Diameter.*—Thick.

*Pattern of growth.*—Straight.

*Color.*—Red-brown (Plate 6 3-F).

*Nodes.*—Size — Enlarged.

*Internodes.*—Medium.

*Tendrils.*—Size — Medium.

*Length.*—Long.

*Position.*—Intermittent.

*Form.*—Long and smooth.

*Shape.*—The tendrils of the new variety are mainly bifurcated. The tendrils of the grapevine of U.S. Plant Pat. No. 5,151 are both bifurcated and trifurcated.

Flowers:

*Generally.*—Fertile. From the third to the tenth mode where most of the fruit is borne, the new variety is very fruitful, generally from twenty percent (20%) to forty percent (40%) more fruitful than the "Superior Seedless" grapevine.

*Date of bloom.*—Bloom begins March 25, reaches full bloom on April 1 and last blooms April 5. This is early as compared with the 'Superior Seedless' grapevine which, in side-by-side comparison, first begins to bloom April 5, reaches full bloom April 12 and last blooms April 20. The Brighton 650 grapevine of the subject invention begins blooming March 25, reaches full bloom by April 1 and last bloom is reached by April 5. As compared with the grapevine of U.S. Plant Pat. No. 5,151, the Brighton 650 grapevine has finished blooming before the grapevine of U.S. Plant Pat. No. 5,151 has started blooming. Its first bloom is April 8 and reaches full bloom on April 12. Its last bloom occurs by April 18.

*Stamens.*—Usually five stamen, but occasionally six. Medium in length, filament straight, pollen very abundant and pistil green in color. Ovoid in shape.

LEAVES

Size:

*Generally.*—Medium.

*Average length.*—12.70 cm (5 inches) to 20.32 cm (8 inches).

*Average width.*—10.16 cm (4 inches) to 20.32 cm (8 inches).

*Average thickness.*—Medium.

Form: Round.

*Upwardly disposed surface—color.*—Alfalfa green (Plate 22, 12-H,I).

*Upwardly disposed surface.*—Smooth and glossy.

*Downwardly disposed surface—color.*—Civette green (Plate 22, 8-F,G).

*Downwardly disposed surface.*—Pubescent and cobwebby.

Leaf margin: Dentate.

Petiole:

*Form.*—Globose, flat, sinus and "U" shaped occasionally overlapping.

*Length.*—10.16 cm (4 inches) to 17.78 cm (7 inches).

*Color.*—New leaves are reddish (Plate 6, 3-F). Leaf blade yellow to chloratic (Plate 13, 1-K,L) eventually turning green (Plate 22, 12-H,I).

Petiolar sinus:

*Shape.*—Shallow and v-shaped. Medium and overlapping.

Basal sinus: Shallow and medium.

Lateral sinus: Shallow and of medium width.

Nodes: 8 to 13 on upper surface.

Lobes: 3 to 5.

Teeth: Medium width and medium depth. 50 to 60 total teeth.

FRUIT

Maturity when described: Ripe for commercial harvesting and shipment approximately May 25 to June 5 near Thermal in the Coachella Valley of California.

*Season.*—Early — mid season. Approximately eleven days earlier than the "Superior Seedless" grapevine when grown adjacent to each other under similar growing conditions. The Brighton 650 grapevine ripens four to eight days earlier than the grapevine of U.S. Plant Pat. No. 5,151 when grown in the same growing area.

Storage quality: Good.

Keeping quality: Very good.

Shipping quality: Excellent. Little to no shatter.

Eating quality: Excellent.

Cluster:

*Size.*—Medium to Large.

*Numbers.*—Two to five per cane.

*Average cluster weight.*—1½ lbs to 2½ lbs. The grapevine of U.S. Plant Pat. No. 5,151 has an average cluster weight of 1 lb.

*Cluster shape.*—Medium in length and broad in width, roundish to tapering, double-shouldered of irregular form and loose to medium in density.

*Peduncle.*—Medium. 2.54 cm (1 inch) to 3.81 cm (1½ inches) in length. 6.78 cm (⅜ inches) to 2.90 cm (⅞ inches) in width. Green lignification. Warts.

*Peduncle—thickness.*—Thick.

Brush: Medium to Long. Yellow in coloration (Plate 11, 1-K).

Berry:

*Generally.*—Variable. Oval. Strongly or medium adherent.

Berry—size.—Medium to large. Length 0.0246 cm (1/16 inch ) to 0.1312 cm (3/16 inch). The average berry size of the grapevine of U.S. Plant Pat. No. 5,151 is smaller than that of the Brighton 650 grapevine of the subject invention.

*Average number of berries per cluster.*—125 to 200. The grapevine of U.S. Plant Pat. No. 5,151 averages 125 berries per cluster.

*Berry color.*—Generally — Yellow green (Plate 13, 1-K,L) to amber white (Plate 11, 1-F).

*Berry skin.*—Generally — Thick, tough and adheres to pulp.

*Bloom.*—Medium.

Flesh:

*Appearance.*—Greenish and translucent (Plate 9, 1-E).

*Texture.*—Meaty, soft and tender. Firm and crisp.

*Juice production.*—Medium and colorless (Plate 9, 1-B).

*Flavor.*—Sweet, slight musky taste, subacid. Best eaten at 15.5 to 16.5 bricks and 0.54 sugar acid content on or about May 25 to June 25.

Seeds: Seedless.

Overall quality: Best to very good.

Use: Fresh table. Raisins — Special, large and chewy.

Resistance to disease: Mildew susceptible.

Although the new variety of grapevine possesses the described characteristics noted above as a result of the growing conditions prevailing near Thermal in the Coachella Valley of California, it is to be understood that variations of the usual magnitude and characteristic incident to changes in growing conditions, irrigation, fertilization, pruning, pest control and the like are to be expected.

Having thus described and illustrated my new variety of grapevine, what I claim as new and desire to be secured by Plant Letters Patent is:

1. A new and distinct variety of grapevine substantially as illustrated and described and which is somewhat remotely similar to the "Superior Seedless" grapevine from which it is derived, but from which it is distinguished principally as to novelty by producing larger, rounder berries and bunches with longer shoulders when grown under the same growing conditions and which are mature for harvesting and shipment approximately May 25 in the Coachella Valley of California, or about eleven days earlier than the "Superior Seedless" grapevine and about four to eight days earlier than the grapevine of U.S. Plant Pat. No. 5,151.

* * * * *

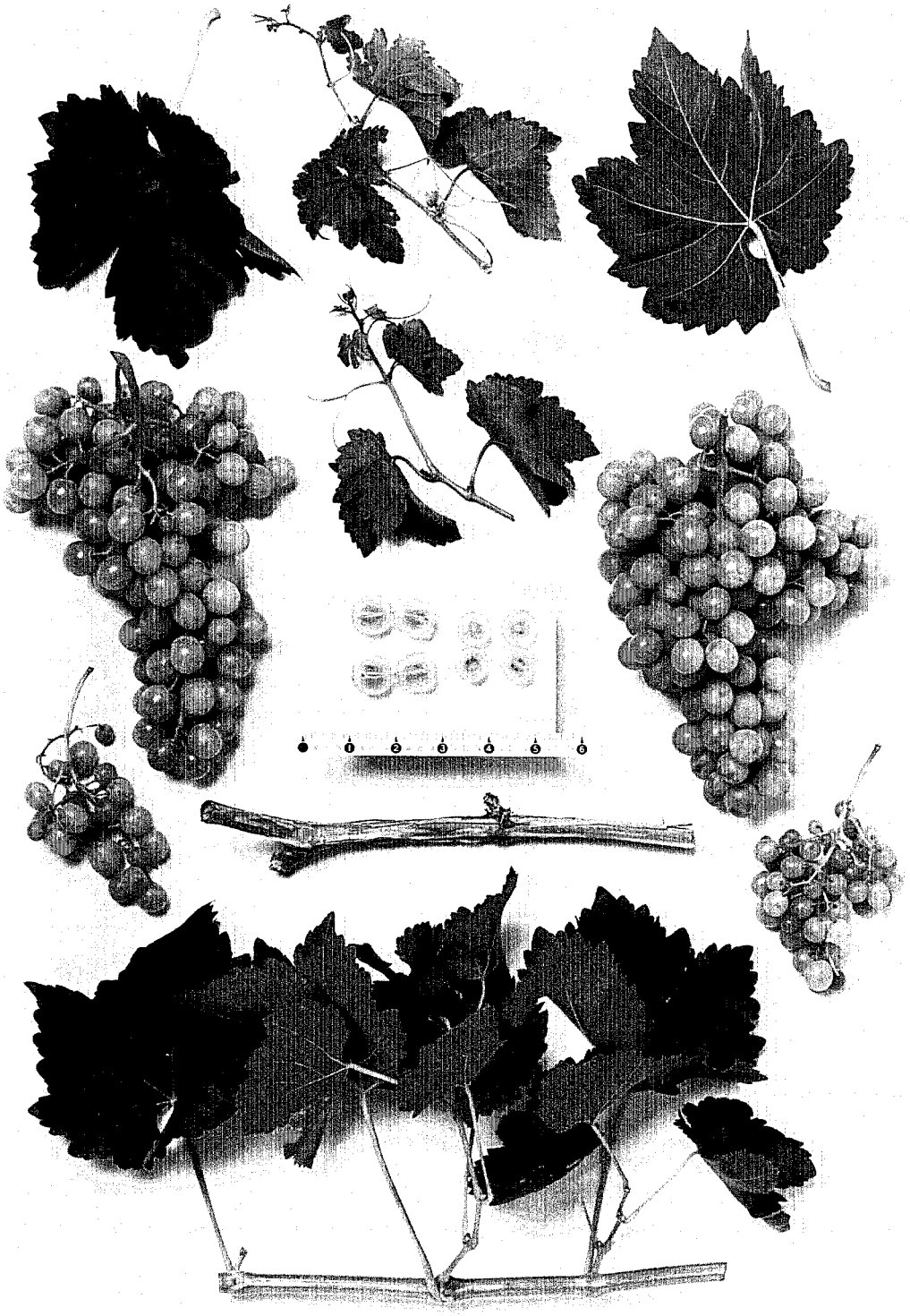

UNITED STATES PATENT AND TRADEMARK OFFICE

CERTIFICATE OF CORRECTION

PATENT NO. : Plant 8,499

DATED : DECEMBER 14, 1993

INVENTOR(S) : HOWARD B. KECK, JR.

It is certified that error appears in the above-identified patent and that said Letters Patent is hereby corrected as shown below:

Column 3, Line 3, delete "grapewine." and substitute "grapevine."

Signed and Sealed this

Twenty-first Day of June, 1994

Bruce Lehman

*Attest:*

BRUCE LEHMAN

*Attesting Officer*

*Commissioner of Patents and Trademarks*